US006360116B1

(12) United States Patent
Jackson, Jr. et al.

(10) Patent No.: US 6,360,116 B1
(45) Date of Patent: Mar. 19, 2002

(54) BRACHYTHERAPY SYSTEM FOR PROSTATE CANCER TREATMENT WITH COMPUTER IMPLEMENTED SYSTEMS AND PROCESSES TO FACILITATE PRE-OPERATIVE PLANNING AND POST-OPERATIVE EVALUATIONS

(75) Inventors: Theodore Ronald Jackson, Jr.; Kevin Stewart Spetz; William Thang Katz, all of Charlottesville; John Wingate Snell, Great Falls; J. Peter Markush, Charlottesville, all of VA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 6 days.

(21) Appl. No.: 09/258,280

(22) Filed: Feb. 26, 1999

Related U.S. Application Data

(60) Provisional application No. 60/076,226, filed on Feb. 27, 1998.

(51) Int. Cl.$^7$ ................................................. A61B 5/05
(52) U.S. Cl. ...................................................... 600/427
(58) Field of Search .............................. 600/407, 411, 600/427, 439, 440; 601/2, 15; 607/2, 100, 101, 102; 424/94.4

(56) References Cited

U.S. PATENT DOCUMENTS

| | | |
|---|---|---|
| 3,783,251 A | 1/1974 | Pavkovich .................. 235/151 |
| 3,871,579 A | 3/1975 | Inamura ..................... 235/198 |
| 3,987,281 A | 10/1976 | Hodes ....................... 235/151.3 |
| 4,802,487 A | 2/1989 | Martin et al. ........... 128/662.06 |
| 4,911,170 A | 3/1990 | Thomas, III et al. ... 128/662.06 |
| 4,917,097 A | 4/1990 | Proudian et al. ....... 128/662.06 |
| 4,958,639 A | 9/1990 | Uchiyama et al. ..... 128/660.03 |
| 5,027,818 A | 7/1991 | Bova et al. ................. 128/653 |

(List continued on next page.)

FOREIGN PATENT DOCUMENTS

| | | |
|---|---|---|
| JP | 10137238 A | 5/1998 |
| WO | WO 97/28743 | 8/1997 |

OTHER PUBLICATIONS

F. Hottier, A. Collet Billon, "3D Echography: Status and Perspective"; NATO ASI Series, vol. F60, 3D Imaging in Medicine, pp. 21–41, 1990.

Riccardo Pini, et al., "Echocardiographic Three–Dimensional Visualization of the Heart"; NATO ASI Series, vol. F60, 3D Imaging In Medicine, pp. 263–274, 1990.

Nath et al.; "Dosimetry of Interstitial Brachytherapy Sources: Recommendations of the AAPM Radiation Therapy Committee Task Group No. 43", *Med. Phys.*, 22(2):209–234 (Feb. 1995): new trailer Novoste™ 1996 Annual Report.

"Hyal Receives First U.S. Patent Allowance for Prevention of Restenosis," *Canada News Wire*, (Dec. 1996).

Fox et al., "Calculated Dose Distribution of Beta–Particle Sources Used for Intravascular Brachytherapy," *International Journal of Radiation Oncology Biology–Physics* (American Society of Therapeutic Radiology and Oncology–ASTRO); vol. 39, No. 2, Supplement, 1997, p. 344.

(List continued on next page.)

*Primary Examiner*—George Manuel
(74) *Attorney, Agent, or Firm*—Lyon & Lyon LLP

(57) ABSTRACT

A system for assisting a user in preparing a brachytherapy pre-operative plan and post-operative evaluation for prostate cancer is disclosed. Image scans are loaded into the system. A user places a matrix on the image scans and outlines the contours the anatomical structures in the image scans. The user then places seeds on the various image scans in a well known manner to treat the prostate cancer. The system provides for real-time isodose calculations as the user edits the pre-operative plan. The user may also view a three-dimensional view of the isodose levels on the anatomical structure, as well as the surface of a given isodose level.

98 Claims, 8 Drawing Sheets

U.S. PATENT DOCUMENTS

| | | | |
|---|---|---|---|
| 5,054,492 A | 10/1991 | Scribner et al. | 128/662.06 |
| 5,099,846 A | 3/1992 | Hardy | 128/653.1 |
| 5,107,839 A | 4/1992 | Houdek et al. | 128/653.1 |
| 5,117,829 A | 6/1992 | Miller et al. | 128/653.1 |
| 5,189,687 A | 2/1993 | Bova et al. | 378/65 |
| 5,205,289 A | 4/1993 | Hardy et al. | 128/653.1 |
| 5,261,404 A | 11/1993 | Mick et al. | 128/653.1 |
| 5,265,610 A | 11/1993 | Darrow et al. | 128/653.1 |
| 5,285,786 A | 2/1994 | Fujii | 128/653.1 |
| 5,297,037 A | 3/1994 | Ifuku | 364/413.15 |
| 5,303,148 A | 4/1994 | Mattson et al. | 364/413.01 |
| 5,305,748 A | 4/1994 | Wilk | 128/653.1 |
| 5,307,816 A | 5/1994 | Hashimoto et al. | 128/660.03 |
| 5,339,812 A | 8/1994 | Hardy et al. | 128/653.1 |
| 5,341,292 A | 8/1994 | Zamenhof | 364/413.13 |
| 5,345,938 A | 9/1994 | Nishiki et al. | 128/660.04 |
| 5,357,550 A | 10/1994 | Asahina et al. | 378/98.5 |
| 5,361,768 A | 11/1994 | Webler et al. | 128/660.09 |
| 5,373,844 A | 12/1994 | Smith et al. | 128/653.1 |
| 5,391,139 A | 2/1995 | Edmundson | 600/7 |
| 5,398,690 A | 3/1995 | Batten et al. | 128/662.05 |
| 5,409,000 A | 4/1995 | Imran | 128/642 |
| 5,418,715 A | 5/1995 | Deasy | 364/413.26 |
| 5,418,827 A | 5/1995 | Deasy et al. | 378/65 |
| 5,454,371 A | 10/1995 | Fenster | |
| 5,458,425 A | 10/1995 | Schweikard | 128/653.1 |
| 5,485,839 A | 1/1996 | Aida et al. | 128/653.1 |
| 5,485,846 A | 1/1996 | Webler et al. | 128/662.06 |
| 5,497,776 A | 3/1996 | Yamazaki et al. | 128/660.09 |
| 5,511,549 A | 4/1996 | Legg et al. | 128/653.1 |
| 5,515,853 A | 5/1996 | Smith et al. | 128/661.01 |
| 5,524,620 A | 6/1996 | Rosenschein | 128/653.1 |
| 5,544,654 A | 8/1996 | Murphy et al. | 128/660.07 |
| 5,562,095 A | 10/1996 | Downey | |
| 5,592,942 A | 1/1997 | Webler et al. | 128/660.09 |
| 5,596,653 A | 1/1997 | Kurokawa | 382/128 |
| 5,596,990 A | 1/1997 | Yock et al. | 128/662.06 |
| 5,618,266 A | 4/1997 | Liprie | 604/21 |
| 5,643,171 A | 7/1997 | Bradshaw et al. | 600/1 |
| 5,647,663 A | 7/1997 | Holmes | 128/653.1 |
| 5,651,043 A | 7/1997 | Tsuyuki et al. | 378/65 |
| 5,651,364 A | 7/1997 | Yock | 128/660.03 |
| 5,660,180 A | 8/1997 | Malinowski et al. | 128/660.03 |
| 5,676,151 A | 10/1997 | Yock | 128/662.93 |
| 5,682,897 A | 11/1997 | Pomeranz | 128/662.06 |
| 5,683,345 A | 11/1997 | Waksman et al. | 600/3 |
| 5,695,751 A | * 12/1997 | Friedman et al. | 424/94.4 |
| 5,701,900 A | 12/1997 | Shehada et al. | 128/662.03 |
| 5,707,332 A | 1/1998 | Weinberger | 600/3 |
| 5,740,225 A | 4/1998 | Nabatame | 378/65 |
| 5,810,007 A | 9/1998 | Holupka | |
| 5,842,473 A | 12/1998 | Fenster | |
| 5,844,241 A | 12/1998 | Liu et al. | 250/363.04 |
| 5,859,891 A | 1/1999 | Hibbard | 378/62 |
| 5,868,673 A | 2/1999 | Vesely | 600/407 |
| 5,870,697 A | 2/1999 | Chandler et al. | 702/179 |
| 5,882,291 A | 3/1999 | Bradshaw et al. | 600/3 |
| 5,897,495 A | 4/1999 | Aida et al. | 600/411 |
| 5,919,135 A | 7/1999 | Lemelson | 600/407 |
| 6,032,678 A | 3/2000 | Rottem | 128/920 |
| 6,038,283 A | 3/2000 | Carol et al. | 378/65 |
| 6,049,729 A | 4/2000 | Cook et al. | 600/407 |
| 6,058,323 A | 5/2000 | Lemelson | 600/408 |
| 6,083,167 A | 7/2000 | Fox et al. | 600/439 |
| 6,095,975 A | 8/2000 | Silvern | 600/439 |
| 6,129,670 A | 10/2000 | Burdette et al. | 600/427 |
| 6,167,296 A | 12/2000 | Shahidi | 600/427 |

OTHER PUBLICATIONS

Moran, John F., "Management of Restenosis: The Challenge for Angioplasty in the 1990's," *Midwest Cardiovascular Institute, Good Samaritan Hospital, Viewpoint* (Winter 1996).

Mintz, Gary S., et al. "Intravascular Ultrasound Predictors of Restenosis After Percutaneous Transcatheter Coronary Revascularization," *J. Am., Coll. Cardiol.*, 27:1678–1687 (1996).

Soares, et al., "Calibration and Characterization of Beta–Particle Sources for Intravascular Brachytherapy," *Med Phys.*, 25(3):339–346 (1998).

EndoSonics, "Oracle® Imaging System IntraCoronary Ultrasound Imaging," pp. 1–3 (website date Dec. 10, 1997).

EndoSonics, "In–Vision™ The Future in IntraCoronary Ultrasound Now . . . " pp. 1–6 (website date Dec. 10, 1997).

Lucia Zamorano, et al., "Image–Guided Stereotactic Centered Craniotomy and Laser Resection of Solid Intracranial Lesions," *Proceedings of the Xth Meeting of the World Society for Stereotactic and Functional Neurosurgery*, Maebashi, Japan (Oct. 1989) *Stereotact Funct Neurosur* (1990); 54+55, pp. 398–403.

T. M. Peters, et al., "Integration of Stereoscopic DSA with Three–Dimensional Image Reconstruction for Stereotactic Planning," *Proceedings of the Xth Meeting of the World Society for Stereotactic and Functional Neurosurgery*, Maebashi, Japan (Oct. 1989) *Stereotact Funct Neurosur* (1990); 54+55, pp. 471–476.

MMS –B3DTUI, Multimedia Medical Systems, dated prior to Feb. 6, 1998.

Therapac Plus, Pinecliff Associates, dated prior to Feb. 6, 1998.

James B. Hermiller, MD, et al., "Quantitative and Qualitative Coronary Angiographic Analysis: Review of Methods, Utility, and Limitations," *Catheterization and Cardiovascular Diagnosis* (1992) 25, pp. 110–131.

* cited by examiner

BRACHYTHERAPY SYSTEM FOR PROSTATE CANCER TREATMENT WITH COMPUTER IMPLEMENTED SYSTEMS AND PROCESSES TO FACILITATE PRE-OPERATIVE PLANNING AND POST-OPERATIVE EVALUATIONS

PRIORITY

This application claims the benefit of U.S. Provisional Application No. 60/076,226, filed Feb. 27, 1998.

FIELD OF THE INVENTION

The invention relates to computer implemented systems and processes to facilitate pre-operative planning and post-operative evaluations of image-guided brachytherapy procedures for treatment of prostate cancer.

BACKGROUND OF THE INVENTION

Brachytherapy procedures for treatment of prostate cancer are well known. Brachytherapy involves treating cancer by precisely locating a plurality of radiation sources inside a human body in a three-dimensional array. The radiation sources generally are "seeds" of radioactive isotopes that are placed in the treatment area according to a seed placement plan.

At least four major steps are performed in a brachytherapy procedure. First, a transrectal ultrasound study of a patient's prostate is made. Creation of the treatment plan is initiated with the capture of transversely oriented transrectal ultrasound images in any one of a plurality of known manners. The images identify the anatomical structures present in the treatment area, and their relative size and location. The volume of the structures is not necessarily calculated. Size assessment using visuals is relative and qualitative.

Second, using the captured images, a pre-operative seed placement plan is developed to determine the desired location of the seeds in a three-dimensional volume. A goal of the placement plan is to enable sufficient doses of radiation to impinge on the structures or portions of structures needing treatment, while attempting to avoid unnecessary amounts of radiation from impinging on other structures or portions of structures in the treatment area. General criteria for establishing seed placement plans is known. In general, the process of generating a seed placement plan involves proposing the location of a plurality of seeds in a three-dimensional volume, and based on the known radiation characteristics of the seeds, calculating the radiation dose levels within the treatment area and displaying isodose lines. Various iterations of the plan may be made in an attempt to optimize the plan. Each iteration requires a new dose calculation which can be time-consuming with known systems.

Once an acceptable plan is approved, the third step is to perform the brachytherapy procedure in a known manner. The seeds are delivered by the use of needles. This typically includes placing a needle guide template over the perineum to assist the physician in placing the seeds in the patient's prostate. The needle guide template is a physical device of known geometry containing holes with half-centimeter spacing. The configuration of the template defines the geometry of the set of possible seed implants. The needle guide template is registered by identifying two known landmarks in the ultrasound image. This accounts for any relative translation, rotation, or scaling of the image study. The physical placement of seeds is effected by loading a plurality of needles each with a plurality of seeds, inserting the needles into the body, and releasing the seeds in an attempt to deliver the seeds according to the plan.

The fourth step is a post-operative evaluation procedure whereby the actual location of the seeds is determined and compared against the plan. To do this, images of the treatment area are taken, such that from the images, the actual seed locations can be identified and compared to the planned location for each seed. Various problems arise in attempting to identify the seeds. In part, this is because to find the three-dimensional array of seeds, the user must look at various image scans. If the length of a seed is greater than the distance between image scans, a seed may appear on multiple image scans. This can give rise to redundant seed identification in adjacent images. If the post-operative evaluation reveals that the actual seed locations varies from the pre-operative plan, corrective action may be necessary.

Computer implemented systems for assisting with some aspects of these procedures are known. Software for one such system is available from Multimedia Medical Systems, the assignee of the present invention, and others. One such system is known as MMS TherpacPLUS Version 6.5. Known systems are useful in assisting with certain aspects of the pre-operative plan and the post-operative evaluation, but have various limitations and drawbacks.

SUMMARY OF THE INVENTION

An object of the invention is to overcome the limitations and drawbacks of prior systems.

Another object of the invention is to provide computer implemented systems and processes to facilitate pre-operative planning and post-operative evaluations in brachytherapy procedures for treatment of prostate cancer including a graphical user interface that guides a user through a plurality of operations relating to pre-operative planning and post-operative evaluations where certain options are displayed or disabled based on previous choices made by the user.

Another object of the invention is to provide computer implemented systems and processes to facilitate pre-operative planning and post-operative evaluations in brachytherapy procedures for treatment of prostate cancer, where real-time image scans may be loaded (e.g., direct video capture from the ultrasound machine or video tape of the procedure, DICOM transfer, or magnetic digitization using a backlit magnetic digitizer tablet ) into the system for use with preparing a pre-operative plan or performing a post-operative evaluation.

Another object of the invention is to provide computer implemented systems and processes to facilitate pre-operative planning and post-operative evaluations in brachytherapy procedures for treatment of prostate cancer including a graphical user interface comprising a plurality of simultaneously displayed, linked windows, also know as a canvas layout, including a relatively larger window for displaying a single, relatively large ultrasound image in a sequence of ultrasound images and a plurality of relatively smaller windows that display thumbnail views of multiple ultrasound images in the sequence of ultrasound images. Selection of an individual image from the thumbnails in the canvas layout is reflected in the single, large window.

Another object of the invention is to provide computer implemented systems and processes to facilitate pre-operative planning and post-operative evaluations in brachytherapy procedures for treatment of prostate cancer that allows a user (e.g., a dosimetrist or physician) to place the seeds (1) individually, (2) in an alternating configuration along a single needle, or (3) using one of a plurality of automatic seed placement routines. The user can modify the seed placement pattern, for example, one generated by an automatic seed placement routine, by overlaying a graphical representation of a needle guide template on each image scan of the anatomical structure, rather than on the entire area of the image scan of the patient, to aid in performing the pre-operative planning and post-operative evaluation.

Another object of the invention is to provide computer implemented systems and processes to facilitate pre-operative planning and post-operative evaluations in brachytherapy procedures for treatment of prostate cancer that enables real-time dose calculations to be performed as a pre-operative plan is altered, and where a dose matrix may be reconfigured over a specified area of the image scans to reduce the memory and time required to perform the calculations.

Another object of the invention is to provide computer implemented systems and processes to facilitate pre-operative planning and post-operative evaluations in brachytherapy procedures for treatment of prostate cancer where anatomical structures in the treatment area can be displayed in a three-dimensional view with solid surface area, and a color-wash of the anatomical structure displays the dose distribution over the surface area with particular isodose values being uniquely displayed.

Another object of the invention is to provide computer implemented systems and processes to facilitate pre-operative planning and post-operative evaluations in brachytherapy procedures for treatment of prostate cancer that reduces redundancy in seed identification during post-operative evaluation by identifying possibly redundant seeds, displaying a list of possibly redundant seeds to the user, and enabling the user to delete, merge or ignore the possibly redundant seeds.

DETAILED DESCRIPTION OF THE EMBODIMENTS OF THE INVENTION

Figure 1:
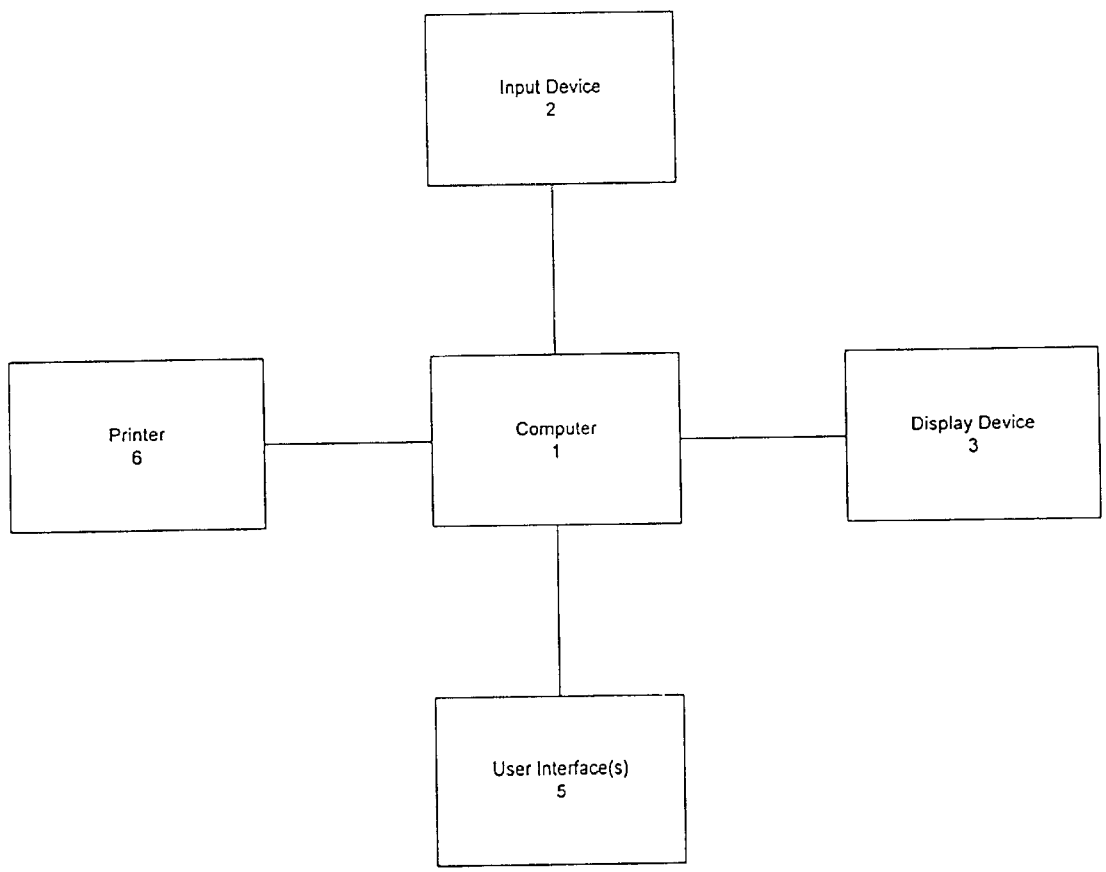
FIG. 1 is a block diagram of the brachytherapy pre-operative planning and post-operative evaluating system.

FIG. 1 is a schematic block diagram depicting an example of a brachytherapy pre-operative planning and post-operative evaluating system according to one embodiment the present invention. As shown, the system comprises a computer 1, an input device 2, a display device 3, a user interface 5 (e.g. keyboard, mouse, etc.), and a printer 6. An input device 2 loads image scans into the computer I for analysis. The user views the image scans and may use the system to manipulate the image scans through the user interface(s) 5. The user may print out image scans and/or data through the printer 6.

Figure 2:
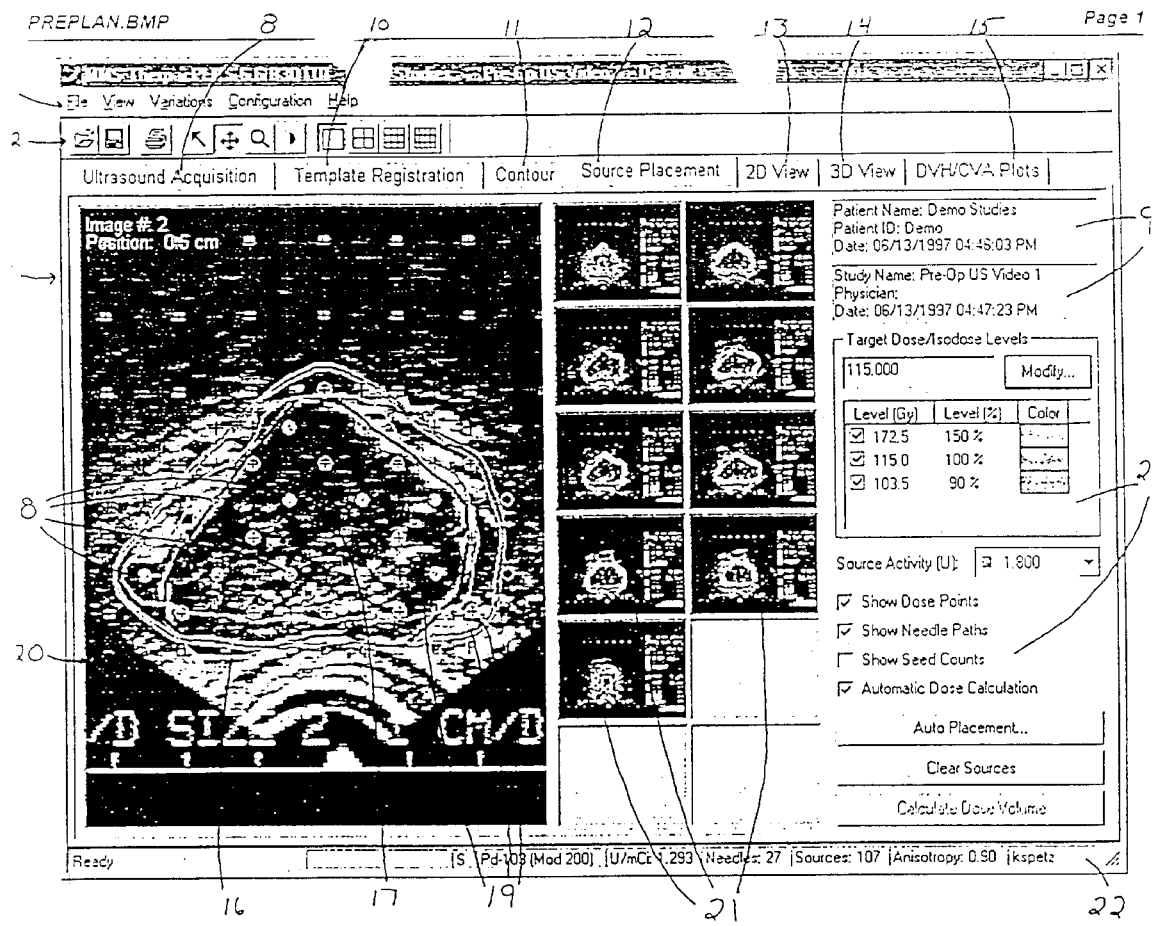
FIG. 2 is an example of a graphical user interface that illustrates various aspects of the invention.

The system assists a user in preparing a pre-operative plan or performing a post-operative evaluation of brachytherapy treatment for prostate cancer. A user first accesses a file, and chooses a type of study (e.g. a pre-operative ultrasound video acquisition study, a pre-operative ultrasound digitization study, a pre-operative ultrasound file import study or other types of studies). A working window 20 such as shown in FIG. 2, appears. The graphical user interface also includes multiple tabs that allow the user to load and manipulate the image scans. The tabs presented depend upon the study type selected. For a given study type certain ones of the displayed tabs may be inactive at certain times to help guide the user through the work-flow steps to be performed. For example, the Source Placement tab 12, the 2D View tab 13, the 3D View tab 14, and the DVH/CVA Plot tab 15 are preferably available for all types of pre-operative plans. A pre-operative video acquisition study may also include an Ultrasound Acquisition tab 8, a Template Registration tab 10, and a Contour tab 11. The pre-operative ultrasound digitization study may also have an Ultrasound Digitization tab available to the user, while a pre-operative ultrasound file import includes an Ultrasound File Load, a Template Registration tab, and a Contour tab. The user activates the tabs as necessary to perform the pre-operative evaluation.

The images may be acquired through various techniques. For example, some techniques may include direct video capture from an ultrasound machine or a video tape of the procedure, DICOM transfer, or magnetic digitization (e.g. using a backlit magnetic digitizer tablet (similar to digitizer tablets used for CAD/CAM applications)).

The user selects a tab to load the image scans into the system. The system window 7 displays one relatively large image in a working window 20, a plurality of other relatively smaller images in thumbnail windows 21, and controls and information about the windows and the plan in other sections of the system window 7. This canvas allows the user to view multiple image scans while designing the pre-operative plan.

In various cases such as an ultrasound file import study or an ultrasound video acquisition study, the user locates a computer generated template over image scans, and uses the user interface 5 and standard software tools to outline the contours of various anatomical structures, such as the prostate, rectum, urethra, and bladder, located within the image scans. Preferably, in all of the studies, the user places seeds on the template to indicate the pre-operative plan. The seeds must be placed on the intersecting grid lines, or nodes, of the template. An auto-placement option is available to the user, where a number of pre-programmed seed placement strategies may be chosen. As the user places seeds, the system can automatically calculate and update the isodose lines located in the working window 20 and the thumbnail windows 21, as well as the information sections of the system window. The user may then view the plan in a two-dimensional view, a three-dimensional view, or through Cumulative Dose Histogram Plots (DVH) and Contiguous Volume Analysis (CVA) plots.

The pre-operative planning starts by selecting a patient. The user initially adds or selects a patient. For a new patient study, the user initially enters information regarding the patient into the system. This information is entered into a series of data entry fields. This data includes name, address, physician etc.

The user is presented with a list of studies associated with a patient (if any). The user may enter a new study, edit study information, or open an existing study. Opening an existing study presents the user with the last saved view of the study. Creating a new study requires the user to enter the type of study used, which may include, for example, ultrasound video acquisition, ultrasound digitization, ultrasound file import, CT digitization, CT file import, and stereo-shift film digitization. The user selects the type of isotope to be used in the procedure (e.g. I-125(6702), I-125 (6711), Pd-103 (Mod 200), etc.). For pre-operative planning, the user selects the template style that matches the type used in the data collection procedure.

The system directs the user through a series of steps in designing the pre-operative brachytherapy plan. The workflow of the system is reinforced by the tab display in each step of the pre-operative planning. All required information for a particular step must be provided or completed in that step before the user can move on. Certain tabs are made inaccessible to the user if necessary information in the initial steps were not completed.

In one example of the work-flow of the system, a user selects the pre-operative ultrasound file import study for the plan. At least the Ultrasound File Load tab, the Template Registration tab, and the Contour tab appear in the system window 7. Only the US File Load tab is available to the user. This requires the user to import the image scans into the system. Once the image scans are complete, the Template Registration tab becomes available to the user. The user then places a template over the anatomical structure(s) of interest in the image scan. The Contour tab becomes available to the user. The user then uses the system to outline the contours of the anatomical structure(s) in the image. The Active Source Placement tab appears and is available to the user. The DVH/CVA Plots tab only becomes available to the user once the first seed is placed. Thus, the user can not place seeds until information on the structures is entered into the system by the user, nor can the user view the plots until at least one seed has been placed.

Figure 7:
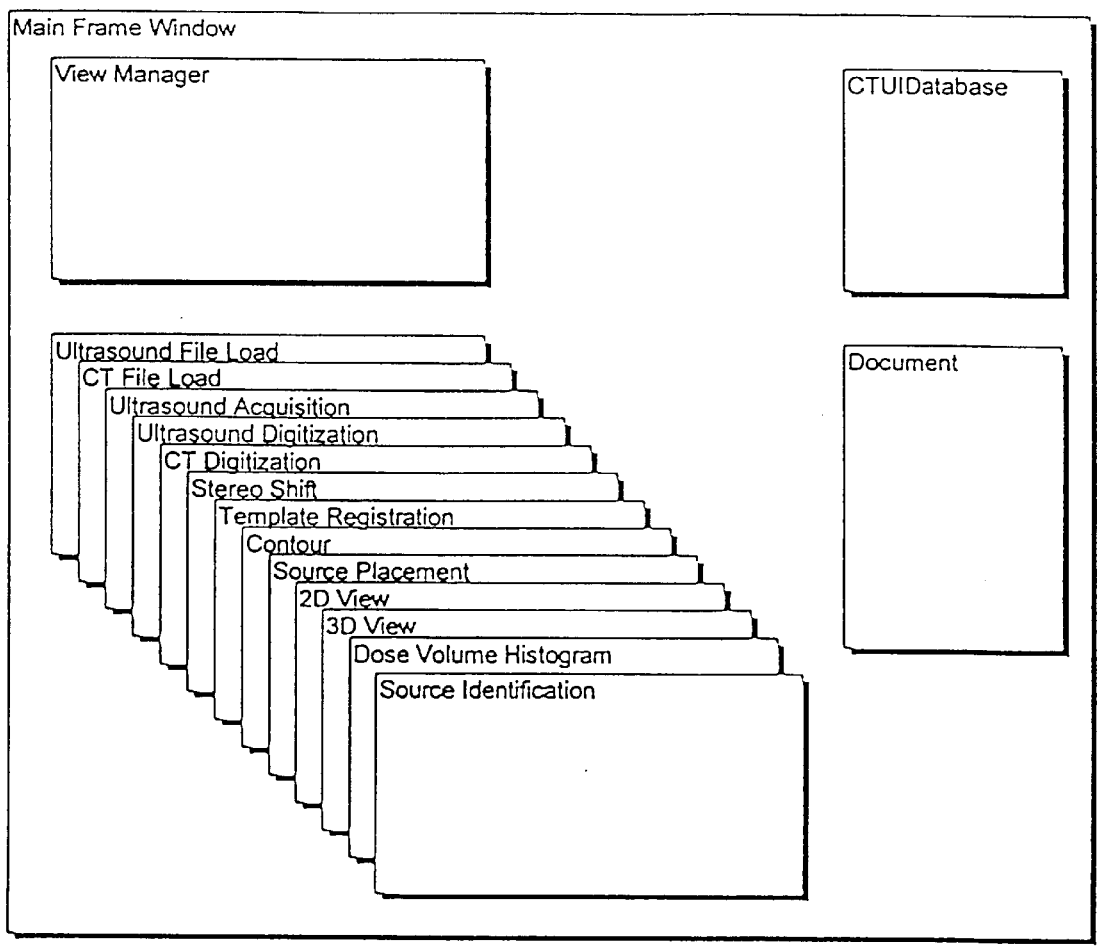
FIG. 7 is a schematic illustration of various views available to a user.
Figure 8:
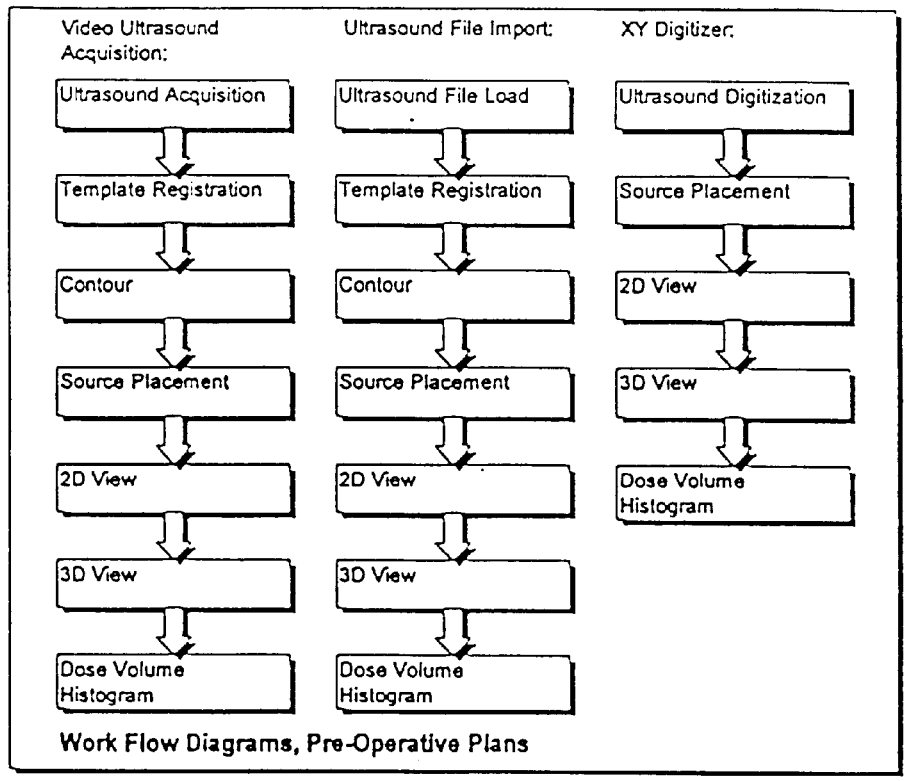
FIG. 8 is an illustration of examples of work-flow options and views available to a user for various pre-operative plans and post-operative evaluations.
Figure 8:
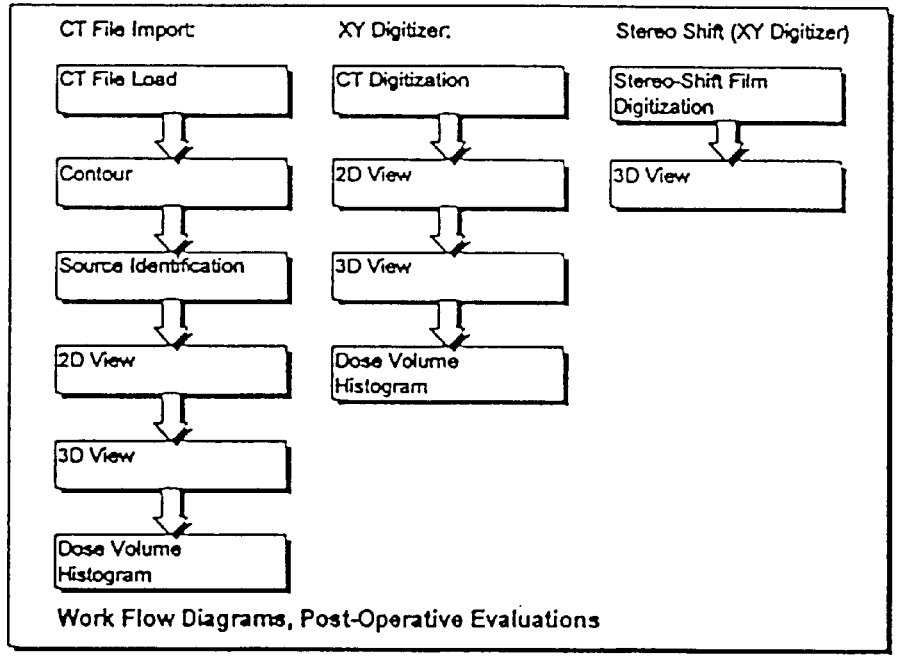

FIG. 7 depicts examples of different views that are available to a user in the form of tabs. Not all of these views will be available at all times, or for all pre-operative plans and post-operative evaluations. FIG. 8 depicts the work-flow for three pre-operative plans and three post-operative evaluations. For example, if the user selects an Ultrasound File Import study in a pre-operative plan, the Ultrasound File Load tab becomes available. After the user has completed the information regarding this tab, the Template Registration tab becomes available. The user must then complete the template registration step before the Contour tab becomes available. This continues throughout the planning. In some instances, more than one tab (i.e. alternative views) may become available to the user after completing the information regarding a previous tab. However, a subsequent tab is not available to the user if information from a previous tab, required for the subsequent tab, is not completed.

The system window 7, shown in FIG. 2, displays a relatively large image. Tabs are located in the system window 7. The example in FIG. 2 shows the Ultrasound Acquisition tab 8, the Template Registration tab 10, the Contour tab 11, the Source Placement tab 12, the 2D View tab 13, the 3D view tab 14, and the DVH/CVA Plots 15. A user activates a tab to work with various aspects of the study. Some tabs enable the user to load image scans from the input device 2. Other tabs allow the user to manipulate the image scans and perform the pre-operative plan of designing the procedure. Not all tabs are available for every study type, or at all times. Only those tabs which are necessary to perform the pre-operative (or post-operative plan) are displayed. For example, if the user initially selected ultrasound video acquisition as the type of study to be used for a patient, a tab for CT digitization would not appear to the user in the system window 7. Thus, the system simplifies the pre-operative planning process for the user by reducing the number of choices to be made.

The patient information section 9 of the system window 7 displays the patient name, the physician, date of the study, and other information. A toolbar 30 is located below the menu bar 31 on the system window 7. The tool bar 30 contains buttons which perform a variety of functions, such as saving the current version of the study, printing the current copy of the reports, enlarging an image scan, changing the canvas layout, or other controls. The availability of these buttons depends upon which tab is currently being used. For example, the button allowing various multiples of image scans to be displayed at the same time is not available when the stereo-shift digitization, 2D View, 3D View, or DVH/CVA Plots tabs are activated. Again, this reduces the number of options confronting the user.

Returning to the example of FIG. 2, ultrasound acquisition is the study type selected. To begin the pre-operative planning, the user selects the Ultrasound Acquisition tab 8 to enter the study images into the system. However, other types of image scan entry, such as CT digitization, ultrasound digitization, and the like may be used with this system. While the type of image scans entered may affect the details of how the system is used, the overall principles remain unaffected.

Note that when the user first accesses the system window 7 to create a new plan, the Ultrasound Acquisition tab 8 is the only one available (active). Any number of related image scans may be loaded into the system for evaluation. As noted above, the system window 7 contains a canvas layout of a working window 20 which displays one relatively large image scan, and a number of thumbnail windows 21, which contain other image scans. The user can use the controls on tool bar 30 to cause the system window 7 to display a canvas layout. The user can display an N×M canvas layout (where N is the number of rows and M is the number of columns in the canvas layout).

The type of input device 2 required will depend upon what type of study is used. Ultrasound digitization plans, CT digitization plans, and stereo-shift evaluations preferably use a digitizer as the input device. A video capture card can be used to input an ultrasound acquisition plan. An ultrasound file import plan or a CT file import plan preferably uses a standard disk drive as the input device.

Once the image scans have been entered, other tabs become available to the user. In the example shown in FIG. 2, the user may then activate the Template Registration Tab 10. The user overlays a graphical representation of a needle guide template over the image scan. This template allows the user to design the pre-operative plan around the desired anatomical structure with a view toward the template structure to be used in the actual procedure.

Once the template has been registered on the image scans of the patient, the user then activates the Contour tab 11. In this mode, the user outlines the shape of various anatomical structures in each image scan, such as the prostate 16, the bladder 17, and other structures. These outlines guide the user in placing seeds when designing the pre-operative plan. The contours also provide information that enables the system to create two-dimensional and three-dimensional views.

The user activates the Source Placement tab 12 and positions seeds on the image scans to design a pre-operative plan. Seeds 18 are placed on nodes of a template on the image scan to indicate their position in relation to anatomical structures 16, 17. Isodose lines 19 are calculated by the system to show the overall dosage contributed by all of the seeds 18 and allow the user to determine what dosage levels an anatomical structure 16, 17 will receive. The user may then add, move or delete a seed 18 to alter the dosage and optimize the treatment.

The system allows a user to define the layout of the image scans in the system window, as well as manipulate the image scans. User manipulation of the image scans includes adjusting the target dose value, placing seeds, working with isodose levels and calculating the dose distribution. The system window 7 displays a canvas layout of a working window 20 with an image scan, a matrix of thumbnail images 21 with additional image scans, a patient information section 9, system status bar 22, and an image information section 23. A particular image may be selected by activating a thumbnail 21. The user may manipulate the image scan in the working window 20 by placing seeds, or controlling the zoom to enlarge shrink the image scans in the working window 20. All manipulation of the image scans occurs in real-time and allows interactive manipulation. For example, placing a seed in one image scan may affect the isodose lines on another image scan.

Image information section 23 allows the user to alter the displays in the working window and the thumbnail windows. The user may choose or change the radiation level corresponding to the isodose lines 18 displayed, the color for each isodose line 19, and the type of seed 18 that is used. The user may also add or delete seeds 18 and which isodose lines 19 are displayed. The image information section 23 also contains areas where the user can enable or disable the automatic dose calculation function, the seed count function, and the function which displays the needle paths. The user has control over the display of the various windows 20, 21 and can more efficiently prepare the pre-operative treatment plan. Additionally, the user may display the image scans in a canvas layout in, for example, a 1×1 canvas, a 2×2 canvas, a 3×3 canvas, or a 3×4 canvas. The size of the canvas layout is limited only by the user interface. A scroll bar is provided to the user if the study contains more image scans than are accounted for in the selected grid.

Another option is the use of an automatic seed placement. The user may select from a number of pre-programmed seed placement strategies. Once the seeds are placed according to these strategies, the user may then alter the placement according to the needs of the current patient. In one example, the user can select a geometric optimization as the pre-planned strategy. If this method is selected, the % packing (0 to 100) field becomes available. The user must then select the percentage of coverage desired. Again, this illustrates how the system can give the user only those choices that are needed for a particular application.

The system status bar 22 contains information about the current study as well as the name of the current user. This information may include the isotope used, the number of needles involved in the pre-operative plan, the number sources, and the seed conversion factor. This information changes as the user adds or removes seeds from the image scan.

An aspect of the present invention is the ability of the system to perform real-time dose calculations. When the user places a seed on the template, the system automatically recalculates the isodose lines and then displays them in the large window 20. The user may also reassign the isodose levels of a seed or group of seeds. The system also automatically recalculates the isodose lines when a seed is added, deleted or moved, or when any of the isotope source types used are altered.

The system calculates the dose delivered to a volume of interest by the seeds. The volume is typically sampled using a grid of points. The dose from a single seed can be described in a dose-versus-distance table. In one embodiment of the invention, the dose-versus-distance table may be precomputed. The total dose to a particular point is calculated by adding the contributions of each seed. The improvements for calculating the dose are explained below.

Dosimetry requires the computer to calculate the dose delivered to a volume, or extent, of interest. The volume is typically sampled using a grid of points. One point is placed every x millimeters where x is the resolution of sampling. We refer to the points in the volume as a dose volume since the dose is calculated at each sample point. The dose from a single seed can be described in a dose-versus-distance table derived from empirical measurement of each radioactive source. The total dose to a particular tissue position is calculated by adding together the contribution of each source. The dose volume is typically updated either by recomputing using a list of radioactive sources or by incrementally updating when a source is added or removed. Isodose lines, which may be selected for display by a user, are calculated based on the dose received by the points. Thus, according to an embodiment of the invention, isodose lines are created from the calculated dosage at points on the grid, with the dosage received by the area between the points on the grid being interpolated based on the neighboring points.

The present invention uses a number of methods to reduce the computational time required to update the dose volume. All of the methods attempt to minimize the amount of computation within the innermost loop which iterates through points in the dose volume along an axis. When recomputing an entire dose volume based on the list of sources, the system uses an outer loop which goes through each source in the list.

One method for removing computation from the innermost loop is to use precomputation of dose using distance as a parameter. Precomputation occurs once during loading of data for a radioactive source, before any source is placed by the user. This results in an array of doses where the distance is used to index into the precomputed dose.

One method to compute the distance between two points is to use the Pythagorean theorem. For a three dimensional matrix, this involves three subtractions, three multiplication's, two additions, and a square root. This method is slow and requires the use of a lot of memory.

A more efficient way to calculate the distance between two points is to calculate iteratively. In order to visit each point in the dose volume, three loops are used, one for passing along each axis in three dimensions. The outermost loop iterates through points parallel to the z-axis. The middle loop iterates through points parallel to the y-axis. The innermost loop steps through each point parallel to the x-axis. At each step in each of the loops, both the direction and the magnitude of the change in position are known. These iterative values can be used to change distance calculation to allow an iterative calculation of the squared distance in the innermost loop. Instead of all the operations required for a distance calculation using the Pythagorean theorem, only two additions in the innermost loop and an assignment in the middle and outer loops to calculate a squared distance are needed. Removing the square root operation also results in a major increase in speed.

Some problems are created when using the squared distance as an index into the dose-versus-distance tables. One problem is the required conversion of the distance into an integer values suitable for array indexing. Typically, conversion of floating-point numbers to integers takes a relatively long time on general computer systems. A second problem involves the memory requirements of an array which covers the range of distances used in dosimetry at reasonable precision. For example, to cover a 15 centimeter span with ½ millimeter resolution requires only 300 values if the distance is used as a parameter. However, squared distances are used, the required array size will grow exponentially as the covered distance increases. In the example above, an array of 300×300 (or 90,000) values is required to cover distances to 225 squared centimeters. Also, if the resolution of the arrays is not fine enough, the system will have to use interpolation to compute the dose at distances between dose-versus-distance tables entries.

According to an embodiment of the invention, the system preferably uses three dose-versus-squared distance arrays. The first array is the highest resolution and handles small distances, for example of up to one centimeter. The second array handles slightly larger distances, for example just beyond one centimeter, while the third array handles larger distances. The use of three arrays allows the precision to be increased at the smaller distances while decreasing the array size (through decreased precision) for the larger distances. According to another embodiment of the invention, the system preferably uses two dose-versus-squared distance arrays. A first array has a higher resolution, and handles distances within small, predetermined distance, while a second array handles distances beyond the predetermined distance. This system works because dose falls off more gradually at larger distances and the actual precision is the square root of the squared distance precision. Use of multiple precomputed arrays limits the memory requirements while still allowing accurate calculation of dose at larger distances.

One time costly operation is the conversion of floating-point numbers to integers suitable for array indexing. This conversion can be bypassed by using fixed-numbers since distances are then held as integers. Fixed-point distances can be used as indices by simply shifting away mantissa and using the integer component for indexing.

Fixed-point arithmetic is also faster for older generation CPU's due to the superior integer arithmetic speeds compared to floating-point arithmetic. In future generations of CPUs, the floating-point speeds may approach and surpass integer arithmetic speeds. However, many of those processors may have parallel pipelines which handle floating-point operations at the same time as integer Dose values within the dose volume are held as floating-point values and dose entries in the precomputed arrays, while indexed using integers, are floating-point values as well. By using fixed-point distance calculations, the indexed dose values can be added to the dose volume using a floating-point operation at the same time that the squared distance for the next point is calculated using integer arithmetic. Therefore, the innermost loop permits the use of parallel pipelines for both integer and floating-point operations.

The dose matrix used for calculating the isodose levels is a three-dimensional grid that can be configured to encompass, for example, 1) the needle guide template (when the user is performing pre-operative planning); 2) all seeds in the image scans; or 3) the prostate. A dose matrix has an extent (or volume), and a resolution. The resolution determines the spacing of the points in the three-dimensional grid. The dose matrix can also be reconfigured to encompass a selected anatomical structure when the system is calculating the dose volume histogram and the contiguous volume analysis. By reconfiguring the dose matrix around a selected figure, the system can make use of the three arrays to speed the calculations. The size of the dose matrix is reduced, the amount of memory required to perform the dose calculations is reduced and the dose calculation times are reduced. Additionally, the resolution around the seeds is not effected.

Reconfiguring the dose matrix may be used when calculating dosage for DVH/CVA plots. A user may select a specific anatomical structure. The dose matrix may be dynamically and automatically reconfigured on the selected anatomical structure. Using dose-versus-squared distance arrays, dosage received by points in the dose matrix may be calculated. The DVH/CVA of the anatomical structure, may be displayed. In another embodiment of the invention, the dose matrix may be reconfigured by a user. Other embodiments may also be used.

Another important function of the present invention is the ability of the user to create multiple variations of a seed plan for a single patient. Rather than have to open a new file for every seed plan, the user may create, store, and recall different variations of a seed plan. Thus, the user would not have to save each particular seed plan, and could experiment with other seed plans without having to reopen existing plans.

Figure 5:
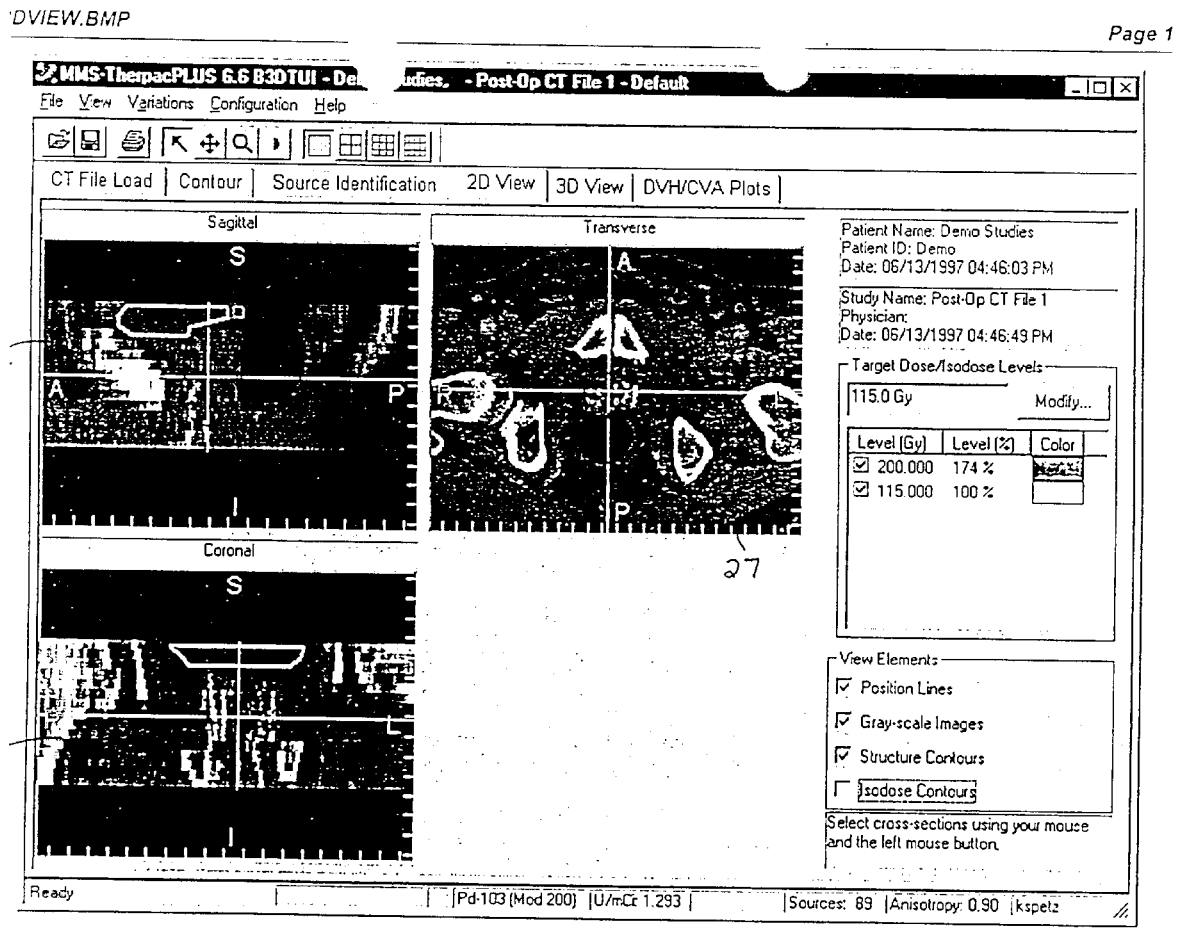
FIG. 5 is an example of a graphical user interface that illustrates the isodose levels for anatomical structures in three orthogonal views, each in two-dimensional form.

After the desired pre-operative plan has been designed, the user may then select the 2D View tab 13 to view the anatomical structures and isodose lines. FIG. 5 displays the two-dimensional views of the anatomical structures. The image 25 displays the sagittal view of the anatomical structures, image 26 displays the coronal view of the anatomical structures, and image 27 displays the transverse view of the anatomical structures. These views are orthogonal to each other. Thus, the user can view the anatomical structures from three different positions.

Figure 6:
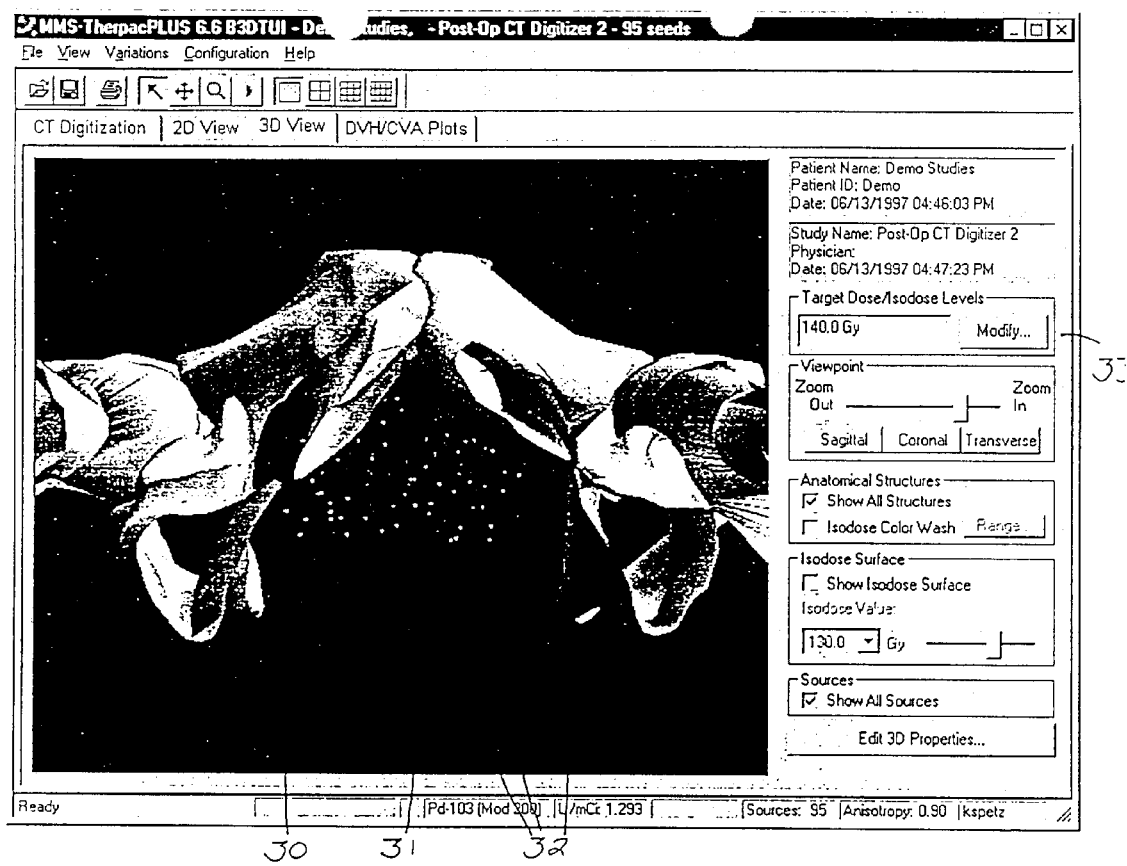
FIG. 6 is an example of a graphical user interface that illustrates a three-dimensional view of the surface area of a particular isodose value in relation to the anatomical structures, as well as the actual location of the seeds, in a post-operative view.

The user may also activate the 3D View tab 14. FIG. 6 displays a three-dimensional view of two anatomical structures 30, 31, along with the seeds 32. The user may move the anatomical structures so as to view it from different positions in the two-dimensional view (e.g. sagittal, coronal, and transverse). The surface of the three dimensional anatomical structures are displayed, allowing shading to aid the user in determining the shape of the structure. The color of the surface of the anatomical structure or portions of the surface indicates the isodose that the structure surface or portion is receiving. A user may also use this feature to see a three-dimensional view of an isodose surface work area. The user can view what areas have a given isodose level. Another image information section 33 of the system window 7 allows the user to manipulate the data and image scans displayed. Again, the user may, for example, change the value of the isodose surfaces 19 shown and perform other control functions.

The DVH/CVA Plots tab 15 enable the user to determine the effectiveness of the pre-operative plan designed. Activating the DVH/CVA Plots tab 15 allows the user to view either a cumulative dose volume histogram or a contiguous volume analysis. A DVH displays a plot of the structure volume that receives a particular dose, e.g., what percentage of the volume of the structure receives a given dose of radiation. A CVA displays a plot of the homogeneity of a radiation dose rate for a target volume, e.g., what actual volume (either total or contiguous) receives a given does of radiation.

After viewing the details of the pre-operative plan, the user may then print out reports to assist in carrying out the prostate cancer treatment plan during the procedure.

Post-Operative Evaluations

The system provides a post-operative evaluation option which allows the user to evaluate the effectiveness of the procedure in carrying out the pre-operative plan. When selecting the study type, the user preferably must select a post-operative study type. The user then follows the same procedures in opening the patients file, loading raw data, and contouring structures.

The user then identifies seeds that are visible in the image scan on the screen. This procedure is similar to placing seeds in the pre-operative planning, except that the seeds are identified in accordance with their actual location in the image scan. The transverse image 27 in FIG. 5 is representative of how seeds might look when using the system. The system calculates the isodose lines for the actual seed configuration. The user may then use the same tools as in the pre-operate plan to determine the effect of the seeds. These tools include multiple windows with the main window, as well as both the two-dimensional and the three-dimensional views.

The post-operative mode of the system contains a redundancy correction function which works to eliminate possible duplicate seeds. Generally, a post-operative evaluation consists of multiple image scans. If the dimensions of one seed are larger than the distance between the scans (and other circumstances), it is possible that one seed will appear to be two seeds on two scans. The user may click on each image of the seed and unwittingly indicate too many seeds.

This system preferably uses three algorithms to perform redundancy correction. The algorithms cover detecting redundant seeds, determining the number of replacement seeds, and determining the placement of replacement seeds.

The system's redundant seed detecting algorithm attempts to delete redundant seeds in post-operative evaluations based on CT image data. In order to detect redundancies, the algorithm uses two user-supplied parameters: an in-plane distance and an out-of-plane distance.

The in-plane distance refers to the two-dimensional distance (parallel to the imaging planes) between the seeds on neighboring images. This distance can be though of as the XY distance where the images define the X and Y axes. The out-of-plane distance provides some estimate of the physical length of the seed. Redundant seeds are detected by checking each seed with every other seed. Any two seeds are considered redundant when they are both on adjacent image slices, and would be separated by less than the In-plane distance if they were projected onto the same XY plane.

Figure 3:
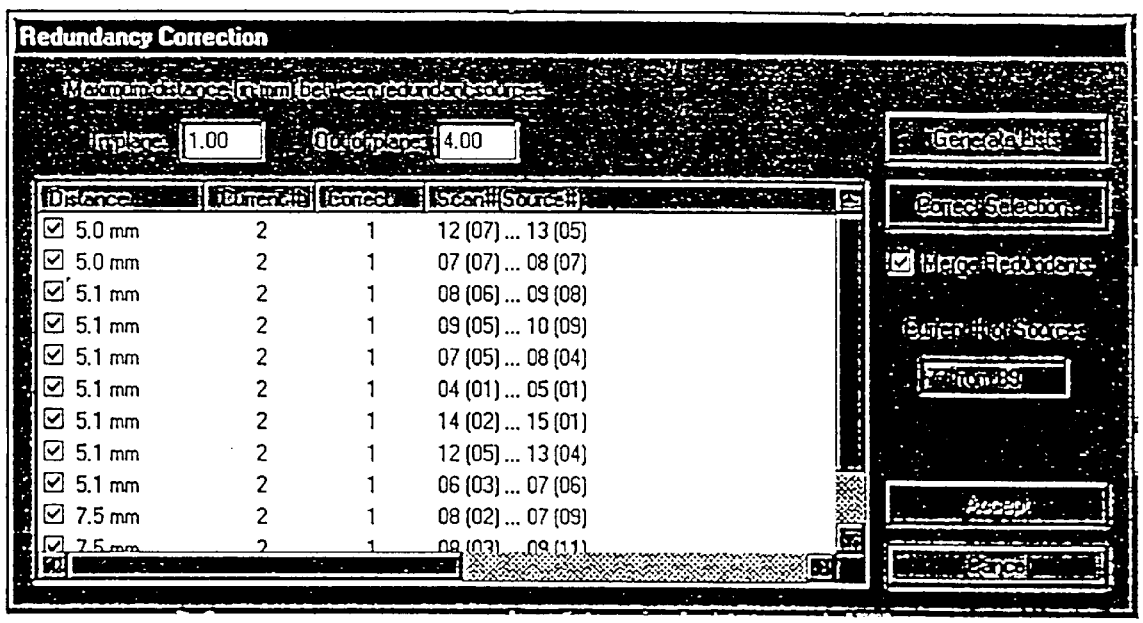
FIG. 3 is an example of a graphical user interface that illustrates various aspects of the redundancy correction feature for seed location in a post-operative evaluation.
Figure 4:
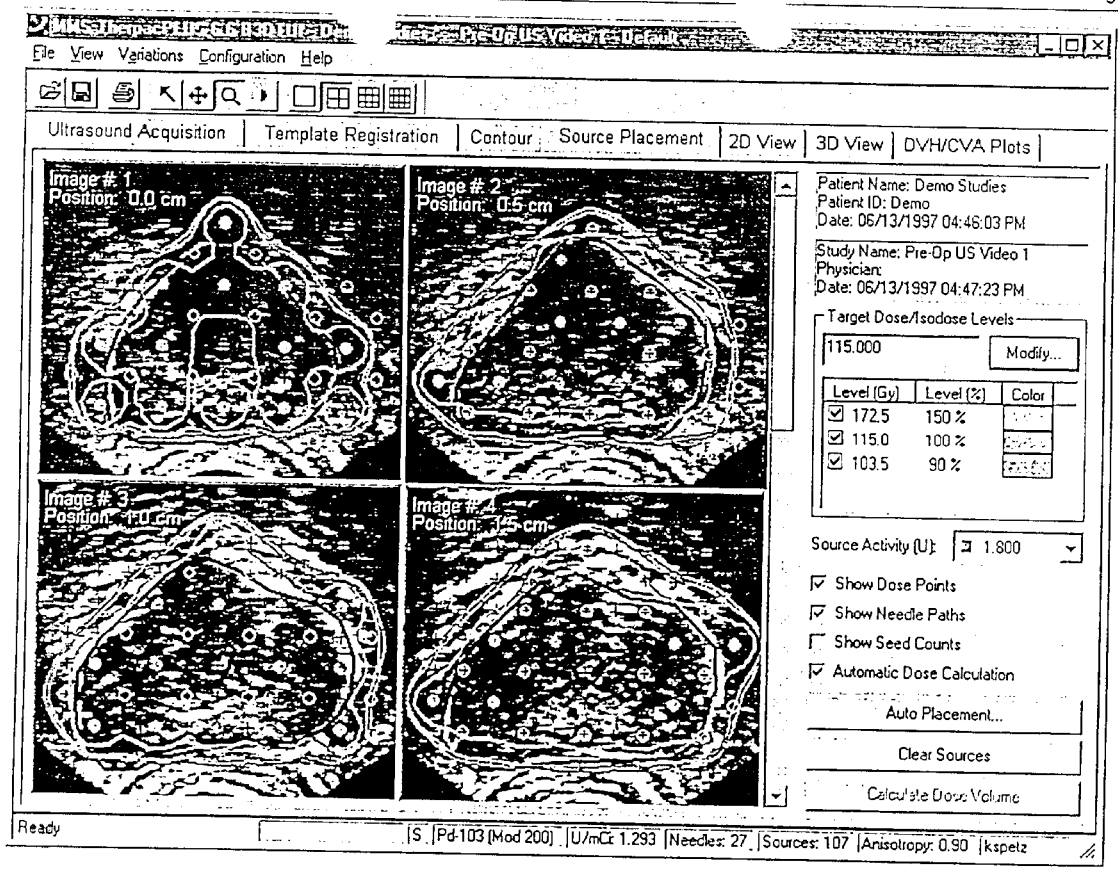
FIG. 4 is an example of a graphical user interface that illustrates a canvas layout of image scans displayed for the user to manipulate when performing the pre-operative planning and post-operative evaluation.

Because medical imaging technology has been decreasing the space between images, it is possible that a single seed will show up in multiple images if the seed is relatively long compared to the image spacing. The system resolves this potential problem by creating lists of possible redundant seeds. FIG. 3 illustrates a listing presented to the user when the redundancy correction function is activated. For example, if seeds A and B are redundant, but seeds B and C are also found to be redundant, a list is created that holds seeds A, B and C. The list shows all the seeds connected through the redundancy criteria. The system then allows the user to replace the seeds in an individual list with a more valid seed description.

The out-of-plane parameter, which provides the estimate of the physical length of the seed, allows the system to estimate how many true seeds are present in a list of possibly redundant seeds. If the largest distance between any two seeds in a list is less than the out-of-plane distance, the list is replaced by a single seed. For example, when a list of redundant seeds consists of A, B and C and the distance between A and C is 4 mm, the system replaces the three seeds listed with one seed if the out-of-plane distance is equal to or less than 4 mm. If the out-of-plane distance is set to 2 mm, the system would preferably replace the three-seed list with two seeds.

The system generates lists of possibly redundant seeds which the user can selectively correct. As the in-plane parameter increases in size, more seeds are considered as possibly redundant. As the out-of-plane parameter increases in size, fewer seeds will be used to replace the identified redundant seeds.

The system uses both the image slice thickness (distance between images) and the out-of-plane distance (estimate of seed thickness) to determine how many seeds should be used to correct a list of redundant seeds for redundancy correction in post-operative evaluations.

The number of scans that can be affected by one seed, $N_1$, is represented by the ceiling function:

$$\text{ceiling}(D_0/D_1)+1$$

$D_0$ is the Out-of-plane distance; $D1$ is the image slice thickness. The ceiling function returns the closest integer greater than or equal to its argument. As $D_0$ approaches zero, it affects at most two images (scans) if it is placed exactly between those two images.

In a list of redundant seeds, the system calculates the maximum distance between any two of the seeds, $D_{MAX}$. The number of replacement seeds, n, is computed by the formula:

$$\text{ceiling}(D_{MAX}/(N_1 \times D_1))$$

For example, if two scans are spaced 5 millimeters apart ($D_1$=5.0) and a specified out-of-plane distance is 5 millimeters ($D_0$=5.0). The number of images that can be affected by one seed is 2($N_1$=2). If the maximum distance between any two seeds in a list of redundant seeds is 15 millimeters, the number of replacement seeds is 2 (I=2):

$$n = \text{ceiling}(15.0/10.0) = 2$$

The system allows a user to correct lists of redundant seeds by either deleting or merging seeds. In both cases, the system attempts to spread out the replacement seeds over the distance covered by the list of redundant seeds. With the deletion process, the seeds on lower numbered scans are preferentially retained.

The merge algorithm attempts to locate the replacement seed(s) in a position, often off-slice, that more closely represents their actual position in the implant. Off-plane seeds are shown as either downward pointing triangles, indicating that they are between the current scan and its lower number neighboring scan, or upward pointing triangles, indicating that they are between the current scan and its higher number neighboring scan.

The merge algorithm computes a spacing distance, S, which is the maximum distance between any two of the seeds, $D_{MAX}$, divided by the number of replacement seeds, n:

$$S=D_{MAX}/n$$

The system then places the replacement seed(s) along the distance (0 to $D_{MAX}$) covered by the list of redundant seeds. The replacement seeds are located at these positions until all n seeds are placed:

$$S/2, 3\ S/2, 5\ S/2,$$

The foregoing is not intended to limit the scope of the invention. Rather, it is to illustrate the ideas and inventive principles of the invention. Various alternatives and modifications are within the scope of the invention.

What is claim is:

1. In a computer implemented system for assisting in an interstitial radiation therapy treatment, where the computer receives two-dimensional images of a three-dimensional treatment area and the computer system comprises a display for graphically displaying the two-dimensional images, and a processor for calculating dose throughout a volume and resulting user-selected isodose lines, a method comprising the steps of:
designating the location of a plurality of radiation sources in the three-dimensional treatment area;
automatically calculating dose and the resulting isodose lines resulting from the plurality of radiation sources at the designated locations; and
displaying the isodose lines on the display.

2. The method according to claim 1, wherein the step of automatically calculating dose and user-selected isodose lines comprises the step of using a plurality of precomputed dose-versus-squared distance arrays, each array having a predetermined resolution.

3. The method according to claim 1, wherein the step of automatically calculating dose comprises using a plurality of precomputed dose-versus-squared distance arrays, each array having a predetermined resolution, wherein a first array is used to calculate dose within a predetermined distance from a source and a second array is used to calculate dose at distances beyond the predetermined distance.

4. The method according to claim 1, wherein the step of automatically calculating dose comprises using a plurality of dose-versus-squared distance arrays, each array having a predetermined resolution, wherein the squared distances are represented as fixed-point numbers to speed indexing.

5. The method according to claim 1, further comprising the steps of:
manipulating at least one of the two-dimensional images; and
automatically recalculating isodose lines resulting from the manipulated two-dimensional images.

6. The method according to claim 5, wherein the step of manipulating comprises at least one of the group of deleting radiation sources from designated locations, moving radiation sources from designated locations, and identifying anatomical structures on the two-dimensional images.

7. The method according to claim 1, wherein the two-dimensional images are in sequence, the method further comprising the steps of:

(a) presenting one two-dimensional image in a working window; and
(b) presenting a plurality of two-dimensional images in thumbnail windows; and
wherein the step of designating locations further comprises designating the location of a plurality of radiation sources on a two-dimensional image in the working window.

8. The method according to claim 7, further comprising the step of changing the presentation of one two-dimensional image in a thumbnail window to a presentation in the working window.

9. The method according to claim 7, wherein the step of displaying the isodose lines further comprises displaying isodose lines on the plurality of two-dimensional images in thumbnail windows resulting from designated locations of the plurality of radiation sources on the two-dimensional image in the working window.

10. The method according to claim 1, further comprising the step of providing preliminary information, wherein preliminary information comprises patient information, radiation source information, and template information, and
the step of automatically calculating isodose lines further comprises automatically calculating isodose lines in response to the preliminary information.

11. The method according to claim 1, further comprising the steps of:
configuring a dose matrix on a selected area of a two-dimensional image;
identifying an anatomical structure in the three-dimensional area;
selecting the anatomical structure; and
dynamically and automatically reconfiguring the dose matrix on the selected anatomical structure;
wherein the step of displaying further comprises displaying the DVH/CVA of the selected anatomical structure.

12. The method according to claim 11, wherein the step of automatically calculating dose and user-selected isodose lines comprises the step of using a plurality of precomputed dose-versus-squared distance arrays, each array having a predetermined resolution.

13. A computer implemented system for assisting in an interstitial radiation therapy treatment, the system comprising:
means for receiving a plurality of two-dimensional images corresponding to a three-dimensional treatment area;
means for designating the location of a plurality of radiation sources on the two-dimensional images;
means for automatically calculating dose throughout a volume and resulting user-selected isodose lines resulting from the plurality of radiation sources at the designated locations; and
means for displaying the isodose lines.

14. The system according to claim 13, wherein the calculating means automatically calculates dose and user-selected isodose lines using a plurality of dose-versus-squared distance arrays, array having a predetermined resolution.

15. The system according to claim 13, wherein the calculating means automatically calculates dose using a plurality of precomputed dose-versus-squared distance arrays, each array having a predetermined resolution, wherein a first array is used to calculate dose within a predetermined distance from a source and a second array is used to calculate dose at distances beyond the predetermined distance.

16. The method according to claim 13, wherein the step of automatically calculating dose comprises using a plurality of dose-versus-squared distance arrays, each array having a predetermined resolution, wherein the squared distances are represented as fixed-point numbers to speed indexing.

17. The system according to claim 13, wherein:
means for manipulating at least one of the two-dimensional images; and
the calculating means automatically recalculates dose and user-selected isodose lines resulting from the manipulated two-dimensional images.

18. The system according to claim 17, wherein manipulating a two-dimensional image comprises at least one of the group of deleting radiation sources from a designated location, moving radiation sources from designated locations, and identifying anatomical structures on the two-dimensional images.

19. The method according to claim 13, wherein the two-dimensional images are in sequence, the system further comprising:
(a) means for presenting one two-dimensional image in a working window; and
(b) means for presenting a plurality of two-dimensional images in thumbnail windows; and
wherein designating locations further comprises designating the location of a plurality of radiation sources on the two-dimensional image in the working window.

20. The system according to claim 19, further comprising means for changing the presentation of one two-dimensional image in a thumbnail window to a presentation in the working window.

21. The system according to claim 19, wherein displaying the isodose lines further comprises displaying isodose lines on the plurality of two-dimensional images in thumbnail windows resulting from the plurality of radiation sources at designated locations on the two-dimensional image in the working window.

22. The system according to claim 13, further comprising means for providing preliminary information, wherein preliminary information comprises patient information, radiation source information, and template information, and
wherein automatically calculating dose and the resulting user-selected isodose lines further comprises automatically calculating isodose lines in response to preliminary information.

23. The system according to claim 13, further comprising:
means for configuring a dose matrix on a selected area of a two-dimensional image;
means for identifying an anatomical structure in the three-dimensional area;
means for selecting the anatomical structure; and
means for dynamically and automatically reconfiguring the dose matrix on the selected anatomical structure;
wherein displaying further comprises displaying the DVH/CVA of the selected anatomical structure.

24. The system according to claim 13, wherein automatically calculating dose and user-selected isodose lines comprises the step of using a plurality of precomputed dose-versus-squared distance arrays, each array having a predetermined resolution.

25. In a computer implemented system for assisting in an interstitial radiation therapy treatment, where the computer receives two-dimensional images of a three-dimensional treatment area and the computer system comprises a display for graphically displaying the two-dimensional images, and a processor for calculating isodose lines, a method comprising the steps of:
providing preliminary information, wherein preliminary information comprises a study type;
presenting to a user a graphical user interface to create an interstitial radiation therapy treatment plan, where the graphical user interface guides a user through a plurality of steps relating to the plan and where certain steps are displayed or disabled based on previous choices made by the user.

26. The method according to claim 25, wherein the study type is an ultrasound based study, and further comprising the steps of:
identifying anatomical structures on the two-dimensional images;
designating the location of a plurality of radiation sources in the three-dimensional treatment area;
calculating isodose lines resulting from the plurality of radiation sources at the designated locations; and
displaying the isodose lines on the display.

27. The method according to claim 26, further comprising the step of registering a template on the two-dimensional images.

28. The method according to claim 26, wherein displaying the isodose lines on the display further comprises:
displaying the isodose lines on the two-dimensional images;
displaying a three-dimensional image based on the identified anatomical structures, designated locations of radiation sources, and three-dimensional isodose surfaces; and
displaying a dose histogram.

29. The method according to claim 25, wherein the study type is an digitizer based study, and further comprising the steps of:
designating the location of a plurality of radiation sources in the three-dimensional treatment area;
calculating isodose lines resulting from the plurality of radiation sources at the designated locations; and
displaying the isodose lines on the display.

30. The method according to claim 29, wherein displaying the isodose lines on the display further comprises:
displaying the isodose lines on the two-dimensional images;
displaying a three-dimensional image of an anatomical structure, designated locations of radiation sources, and three-dimensional isodose surfaces; and
displaying a dose histogram.

31. The method according to claim 25, wherein preliminary information further comprises patient information, radiation source information, and template information.

32. The method according to claim 25, wherein the graphical user interface further provides tabs to guide a user through various steps relating to the plan, and the tabs are grayed out based on previous choices made by the user.

33. In a computer implemented system for assisting in an interstitial radiation therapy treatment, where the computer receives two-dimensional images of a three-dimensional treatment area and the computer system comprises a display for graphically displaying the two-dimensional images, and a processor for calculating isodose lines, a method comprising the steps of:
providing preliminary information, wherein preliminary information comprises a study type;

presenting to a user a graphical user interface to create an interstitial radiation therapy treatment evaluation, where the graphical user interface guides a user through a plurality of steps relating to the evaluation and where certain steps are displayed or disabled based on previous choices made by the user.

34. The method according to claim 33, wherein preliminary information further comprises patient information, and radiation source information.

35. The method according to claim 33, wherein the graphical user interface further provides tabs to guide a user through various steps relating to the evaluation, and the tabs are grayed out based on previous choices made by the user.

36. The method according to claim 33, wherein the study type is CT file based study, and further comprising the steps of:
   identifying anatomical structures on the two-dimensional images;
   identifying the location of a plurality of radiation sources in the three-dimensional treatment area;
   calculating isodose lines resulting from the plurality of radiation sources at the designated locations; and
   displaying the isodose lines on the display.

37. The method according to claim 36, wherein displaying the isodose lines on the display further comprises:
   displaying the isodose lines on the two-dimensional images;
   displaying a three-dimensional image based on the identified anatomical structures, designated locations of radiation sources, and three-dimensional isodose surfaces; and
   displaying a dose histogram.

38. The method according to claim 33, wherein the study type is digitizer based, further comprising the steps of:
   displaying the isodose lines on the two-dimensional images;
   displaying a three-dimensional image of an anatomical structure, designated locations of radiation sources, and three-dimensional isodose surfaces; and
   displaying a dose histogram.

39. A computer implemented system for assisting in an interstitial radiation therapy treatment, the system comprising:
   means for receiving a plurality of two-dimensional images of a three-dimensional treatment area;
   means for providing preliminary information, wherein the preliminary information comprises a study type; and
   means for presenting to a user a graphical user interface to create an interstitial radiation therapy treatment plan, where the graphical user interface guides a user through a plurality of steps relating to the plan and where certain steps are displayed or disabled based on previous choices made by the user.

40. The system according to claim 39, wherein the study type is an ultrasound based study, and further comprising:
   means for identifying anatomical structures on the two-dimensional images;
   means for designating the location of a plurality of radiation sources in the three-dimensional treatment area;
   means for calculating isodose lines resulting from the plurality of radiation sources at the designated locations; and
   means for displaying the isodose lines on the display.

41. The system according to claim 40, further comprising means for registering a template on the two-dimensional images.

42. The system according to claim 40, wherein displaying the isodose lines further comprises:
   displaying the isodose lines on the two-dimensional images;
   displaying a three-dimensional image based on the identified anatomical structures, designated locations of radiation sources, and three-dimensional isodose surfaces; and
   displaying a dose histogram.

43. The system according to claim 39, wherein the study type is an digitizer based study, and further comprising:
   means for designating the location of a plurality of radiation sources in the three-dimensional treatment area;
   means for calculating isodose lines resulting from the plurality of radiation sources at the designated locations; and
   means for displaying the isodose lines.

44. The system according to claim 43, wherein displaying the isodose lines further displaying the isodose lines on the two-dimensional images;
   displaying a three-dimensional image of an anatomical structure, designated locations of radiation sources, and three-dimensional isodose surfaces; and
   displaying a dose histogram.

45. The system according to claim 39, wherein preliminary information further comprises patient information, radiation source information, and template information.

46. The system according to claim 39, wherein the graphical user interface further provides tabs to guide a user through various steps relating to the plan, and the tabs are grayed out based on previous choices made by the user.

47. A computer implemented system for assisting in an interstitial radiation therapy treatment, the system comprising:
   means for receiving a plurality of two-dimensional images of a three-dimensional treatment area;
   means for providing preliminary information, wherein the preliminary information comprises a study type; and
   means for presenting to a user a graphical user interface to create an interstitial radiation therapy treatment evaluation, where the graphical user interface guides a user through a plurality of steps relating to the evaluation and where certain steps are displayed or disabled based on previous choices made by the user.

48. The system according to claim 47, wherein preliminary information further comprises patient information, and radiation source information.

49. The system according to claim 47, wherein the graphical user interface further provides tabs to guide a user through various steps relating to the evaluation, and the tabs are grayed out based on previous choices made by the user.

50. The system according to claim 47, wherein the study type is a CT file based study, and further comprising:
   means for identifying anatomical structures on the two-dimensional images;
   means for identifying the location of a plurality of radiation sources in the three-dimensional treatment area;
   means for calculating isodose lines resulting from the plurality of radiation sources at the designated locations; and
   means for displaying the isodose lines on the display.

51. The system according to claim 50, wherein displaying the isodose lines on the display further comprises:
   displaying the isodose lines on the two-dimensional images;
   displaying a three-dimensional image of the identified anatomical structures, designated locations of radiation sources, and three-dimensional isodose surfaces; and
   displaying a dose histogram.

52. The system according to claim 47, wherein the study type is digitizer based study, further comprising:
   means for displaying the isodose lines on the two-dimensional images;
   means for displaying a three-dimensional image of an anatomical structure, designated locations of radiation sources, and three-dimensional isodose surfaces; and
   means for displaying a dose histogram.

53. In a computer implemented system for assisting in an interstitial radiation therapy treatment, where the computer receives a sequence of two-dimensional images of a three-dimensional treatment area, and the computer system comprises a display for graphically displaying the two-dimensional images, and a processor for calculating isodose lines, a method comprising the steps of:
   presenting one two-dimensional image in a working window;
   presenting a plurality of two-dimensional images in thumbnail windows;
   designating the location of a plurality of radiation sources in the three-dimensional treatment area;
   calculating isodose lines resulting from the plurality of radiation sources at the designated locations; and
   displaying the isodose lines on the display.

54. The method according to claim 53, further comprising the step of changing the presentation of one two-dimensional image in a thumbnail window to a presentation in the working window.

55. The method according to claim 53, wherein the step of displaying the isodose lines further comprises displaying isodose lines on the plurality of two-dimensional images in thumbnail windows based on designated locations on the two-dimensional image in the working window.

56. The method according to claim 53, further comprising the steps of:
   manipulating at least one the two-dimensional images; and
   recalculating isodose lines resulting from the manipulated two-dimensional images.

57. The method according to claim 56, wherein the step of manipulating may comprise at least one of the group of deleting radiation sources from designated locations, moving radiation sources from designated locations, and identifying anatomical structures on the two-dimensional images.

58. The method according to claim 53, wherein the step of presenting a plurality of two-dimensional images in thumbnail windows further comprises presenting the sequence of two-dimensional images in thumbnail windows, thereby presenting the three-dimensional treatment area.

59. The method according to claim 53, wherein the step of automatically calculating dose user-selected isodose lines comprises the step of using a plurality of precomputed dose-versus-squared distance arrays, each array having a predetermined resolution.

60. The method according to claim 53, wherein the step of automatically calculating dose comprises using a plurality of precomputed dose-versus-squared distance arrays, each array having a predetermined resolution, wherein a first array is used to calculate dose within a predetermined distance from a source and a second array is used to calculate dose at distances beyond the predetermined distance.

61. The method of claim 53, further comprising the step of providing preliminary information, wherein preliminary information comprises patient information, radiation source information, and template information, and
   the step of calculating isodose lines further comprises calculating isodose lines in response to the preliminary information.

62. A computer implemented system for assisting in an interstitial radiation therapy treatment, the system comprising:
   means for receiving a plurality of two-dimensional images corresponding to a three dimensional treatment area, wherein the two-dimensional images are in sequence;
   means for manipulating the two-dimensional images, wherein manipulating comprises:
      (a) designating one two-dimensional image to be presented in a working window;
      (b) designating a plurality of two-dimensional images to be presented in thumbnail windows; and
      (c) designating the location of a plurality of radiation sources in the three-dimensional area;
   means for calculating isodose lines resulting from the plurality of radiation sources at the designated locations; and
   means for displaying the isodose lines.

63. The system of claim 62, wherein the manipulating further comprises changing the presentation of one two-dimensional image in a thumbnail window to a presentation in a working window.

64. The system according to claim 62, wherein displaying isodose lines further comprises displaying isodose lines on the plurality of two-dimensional images in thumbnail windows based on designated locations on the two-dimensional image in the working window.

65. The system according to claim 62, wherein presenting a plurality of two-dimensional images in thumbnail windows further comprises presenting all of the two-dimensional images in thumbnail windows, thereby presenting the entire three-dimensional treatment area.

66. The method according to claim 62, wherein the step of automatically calculating dose user-selected isodose lines comprises the step of using a plurality of precomputed dose-versus-squared distance arrays, each array having a predetermined resolution.

67. The method according to claim 62, wherein the step of automatically calculating dose comprises using a plurality of precomputed dose-versus-squared distance arrays, each array having a predetermined resolution, wherein a first array is used to calculate dose within a predetermined distance from a source and a second array is used to calculate dose at distances beyond the predetermined distance.

68. The system according to claim 62, further comprising:
   means for recalculating isodose lines resulting from the manipulated two-dimensional images.

69. The system according to claim 68, wherein manipulating further comprises at least one of the group of deleting radiation sources from designated locations, moving radiation sources from designated locations, and identifying anatomical structures on the two-dimensional images.

70. The method of claim 62, further comprising means for providing preliminary information, wherein preliminary information comprises patient information, radiation source information, and template information, and wherein calculating isodose lines further comprises calculating isodose lines in response to the preliminary information.

71. In a computer implemented system for assisting in an interstitial radiation therapy treatment, where the computer receives two-dimensional images of a three-dimensional treatment area and the computer system comprises a display for graphically displaying the two-dimensional images, and a processor for calculating dose throughout a volume and resulting user-selected isodose lines, a method comprising the steps of:

configuring a dose matrix on a selected volume of the three-dimensional area;

identifying anatomical structures on the two-dimensional images;

designating the location of plurality of radiation sources in the three-dimensional area;

dynamically and automatically reconfiguring the dose matrix extent and resolution in the three-dimensional area to cover anatomical structures and sources;

calculating dose and resulting isodose lines resulting from the plurality of radiation sources at the designated locations using the dose matrix;

calculating a DVH/CVA resulting from the plurality of radiation sources using the dynamically and automatically reconfigured dose matrix; and displaying the isodose lines on the display.

72. The method according to claim 71, further comprising the steps of:

selecting an identified anatomical structure; and wherein the step of reconfiguring the dose matrix further comprises reconfiguring the dose matrix on the selected anatomical structure; and the step of displaying further comprises displaying the DVH/CVA of the selected anatomical structure.

73. The method of claim 71, wherein the step of calculating dose and user-selected isodose lines comprises the step of using a plurality of precomputed dose-versus-squared distance arrays, each array having a predetermined resolution.

74. The method according to claim 71, wherein the step of calculating dose comprises using a plurality of precomputed dose-versus-squared distance arrays, each array having a predetermined resolution, wherein a first array is used to calculate dose within a predetermined distance from a source and a second array is used to calculate dose at distances beyond the predetermined distance.

75. The method according to claim 71, further comprising the steps of:

calculating the dose and resulting isodose lines after reconfiguring the dose matrix.

76. The method according to claim 71, further comprising the steps of:

manipulating at least one of the two-dimensional images; and recalculating dose and the resulting isodose lines after manipulating the two-dimensional images.

77. The method according to claim 76, wherein the step of manipulating comprises at least one of the group of deleting radiation sources from designated locations, moving radiation sources from designated locations, and identifying anatomical structures on the two-dimensional images.

78. The method according to claim 71, wherein the two-dimensional images are in sequence, the method further comprising the steps of:

(a) presenting one two-dimensional image in a working window; and (b) presenting a plurality of two-dimensional images in thumbnail windows; and wherein the step of designating locations further comprises designating the location of a plurality of radiation sources on the two-dimensional image in the working window.

79. The method according to claim 78, further comprising the step of changing the presentation of one two-dimensional image in a thumbnail window to a presentation in the working window.

80. The method according to claim 78, wherein the step of displaying the isodose lines further comprises displaying isodose lines on the plurality of two-dimensional images in thumbnail windows resulting from the plurality of radiation sources at designated locations on the two-dimensional image in the working window.

81. The method according to claim 71, further comprising the step of providing preliminary information, wherein preliminary information comprises patient information, radiation source information, and template information, and the step of automatically calculating dose and the resulting isodose lines further comprises automatically calculating the dose and resulting isodose lines in response to the preliminary information.

82. A computer implemented system for assisting in an interstitial radiation therapy treatment, the system comprising:

means for receiving a plurality of two-dimensional images corresponding to a three-dimensional treatment area;

means for configuring a dose matrix on a selected volume of the three-dimensional area;

means for identifying anatomical structures on the two-dimensional images;

means for designating the location of plurality of radiation sources in the three-dimensional area;

means for dynamically and automatically reconfiguring the dose matrix extent and resolution in the three-dimensional area to cover anatomical structures and sources;

means for calculating dose and resulting isodose lines resulting from the plurality of radiation sources at the designated locations using the dose matrix;

means for calculating a DVH/CVA resulting from the plurality of radiation sources using the dynamically and automatically reconfigured dose matrix; and means for displaying the isodose lines.

83. The system according to claim 82, further comprising the steps of:

means for selecting an identified anatomical structure; and wherein reconfiguring the dose matrix further comprises reconfiguring the dose matrix on the selected anatomical structure; and displaying further comprises displaying the DVH/CVA of the selected anatomical structure.

84. The system according to claim 82, wherein calculating dose and user-selected isodose lines comprises using a plurality of precomputed dose-versus-squared distance arrays, each array having a predetermined resolution.

85. The system according to claim 82, wherein calculating dose comprises using a plurality of precomputed doseversus-squared distance arrays, each array having a predetermined resolution, wherein a first array is used to calculate dose within a predetermined distance from a source and a second array is used to calculate dose at distances beyond the predetermined distance.

86. The system according to claim 82, wherein calculating the dose and resulting isodose lines occurs after reconfiguration of the dose matrix.

87. The system according to claim 82, further comprising:
means for manipulating at least one of the two-dimensional images; and
means for recalculating dose and resulting isodose lines after manipulating the two-dimensional images.

88. The system according to claim 87, wherein manipulating comprises at least one of the group of deleting radiation sources from designated locations, moving radiation sources from designated locations, and identifying anatomical structures on the two-dimensional images.

89. The system according to claim 82, wherein the two-dimensional images are in sequence,
the system further comprising:
means for presenting one two-dimensional image in a working window; and
means for presenting a plurality of two-dimensional images in thumbnail windows;
wherein designating locations further comprises designating the location of a plurality of radiation sources on the two-dimensional image in the working window.

90. The method according to claim 89, further comprising means for changing the presentation of one two-dimensional image in a thumbnail window to a presentation in the working window.

91. The method according to claim 89, wherein displaying the isodose lines further comprises displaying isodose lines on the plurality of two-dimensional images in thumbnail windows resulting from the plurality of radiation sources at designated locations on the two-dimensional image in the working window.

92. The method according to claim 82, further comprising means for providing preliminary information, wherein preliminary information comprises patient information, radiation source information, and template information, and
wherein calculating dose and resulting isodose lines further comprises calculating dose and resulting isodose lines in response to the preliminary information.

93. In a computer implemented system for assisting in an interstitial radiation therapy treatment, where the computer receives two-dimensional images of a three-dimensional treatment area and the computer system comprises a display for graphically displaying the two-dimensional images, and a processor for calculating isodose lines, a method comprising the steps of:
designating anatomical structures on the two-dimensional images;
designating the location of a plurality of radiation sources in the three-dimensional treatment area;
constructing a three-dimensional image of at least one anatomical structure's surface based on designated anatomical structures on the two-dimensional images; and
displaying the anatomical three-dimensional image.

94. The method according to claim 93, wherein the step of displaying results further comprises color-coding the surface of the anatomical structure to graphically depict the dosage received by the surface of the anatomical structure, wherein the color of the surface indicates the dosage received at that portion of the surface.

95. The method according to claim 93, wherein the step of displaying further comprises:
designating an isodose level for which to display an isodose surface;
generating a three-dimensional image representing an isodose surface based on the designated isodose level; and
displaying the three-dimensional image.

96. A computer implemented system for assisting in an interstitial radiation therapy treatment, the system comprising:
means for receiving a plurality of two-dimensional images corresponding to a three-dimensional treatment area;
means for manipulating the two-dimensional images, wherein manipulating comprises:
(a) designating anatomical structures on the two-dimensional images; and
(b) designating the location of a plurality of radiation sources in the three-dimensional treatment area;
means for constructing at least one three-dimensional image representing an anatomical surface based on the designated anatomical structures in the two-dimensional images;
means for calculating isodose lines resulting from the plurality of radiation sources at the designated locations; and
means for displaying the anatomical three-dimensional image.

97. The system of claim 96, wherein displaying results further comprises displaying a color-code on the three-dimensional image of the anatomical structure to graphically depict the dosage received by the surface of the three-dimensional image, wherein the color of the surface indicates the dosage received at that portion of the surface.

98. The system of claim 96, wherein manipulating further comprises designating an isodose level to display an isodose surface, the system further comprising means for generating a three-dimensional image representing an isodose surface based on the designated isodose level; and
means for displaying the three-dimensional image.

* * * * *

UNITED STATES PATENT AND TRADEMARK OFFICE
CERTIFICATE OF CORRECTION

| | | |
|---|---|---|
| PATENT NO. | : 6,360,116 B1 | Page 1 of 1 |
| DATED | : March 19, 2002 | |
| INVENTOR(S) | : Theodore Ronald Jackson, Jr. et al. | |

It is certified that error appears in the above-identified patent and that said Letters Patent is hereby corrected as shown below:

<u>Title page,</u>
Item [*] Notice, please replace "6 days" with -- 13 days --
Item [56], References Cited, U.S. PATENT DOCUMENTS, please replace the patent number "5,458,425" with -- 5,458,125 --

<u>Column 4,</u>
Line 5, please replace "computer I" with -- computer 1 --

<u>Column 18,</u>
Line 24, immediately after the word "further", please insert -- comprises: --

Signed and Sealed this

Sixth Day of January, 2004

JAMES E. ROGAN
*Director of the United States Patent and Trademark Office*